United States Patent [19]

Lin

[11] 4,434,248

[45] Feb. 28, 1984

[54] PROCESS FOR PREPARING ALKANOLS FROM SYNTHESIS GAS

[75] Inventor: Jiang-Jen Lin, Round Rock, Tex.

[73] Assignee: Texaco Inc., White Plains, N.Y.

[21] Appl. No.: 426,317

[22] Filed: Sep. 29, 1982

[51] Int. Cl.$^3$ .................. C07C 29/15; C07C 27/06
[52] U.S. Cl. .................. 518/700; 502/154; 502/164
[58] Field of Search .................. 518/700

[56] References Cited

U.S. PATENT DOCUMENTS 4,315,994 2/1982 Knifton .................. 518/701

Primary Examiner—Howard T. Mars
Attorney, Agent, or Firm—Jack H. Park; Richard A. Morgan; Cynthia L. Kendrick

[57] ABSTRACT

This invention concerns a process of making alkanols which comprises reacting a mixture of CO and $H_2$ at a pressure of about 500 psig or greater and at a temperature of at least 150° C. in the presence of a catalyst system comprising a ruthenium-containing compound, a nickel or iron containing compound and a quaternary phosphonium salt, in the presence of an inert, oxygenated solvent.

22 Claims, No Drawings

PROCESS FOR PREPARING ALKANOLS FROM SYNTHESIS GAS

BACKGROUND OF THE INVENTION

1. Field of the Invention

This invention concerns an improved process for preparing alkanols by reaction of oxides of carbon with hydrogen in presence of a catalyst system.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C., or more using a mixture of copper, chromium and zinc oxides as catalyst. A wide variety of catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed. In U.S. Pat. Nos. 4,332,914 and 4,332,915 where the reaction of carbon monoxide and hydrogen is conducted with a ruthenium catalyst and a cobalt, rhenium or manganese co-catalyst dispersed in a low melting quaternary phosphonium salt, a wide spectrum of alkanol and ester product were produced.

One serious problem associated with synthesis gas operations in the past has been the non-selectivity of the product distribution since high activity catalysts generally yield a liquid product containing numerous hydrocarbon materials. Thus, complicated recovery schemes are necessary to separate the desired products and the overall yield of the valuable organic products is low. There is a definite need in the art for a process which will produce alkanols and especially methanol and/or ethanol rich alkanols with a high degree of selectivity from synthesis gas.

This invention therefore is to provide a process of making alkanols by resort to a unique catalyst system which produces said alkanols in good yields and with good selectivity, especially for methanol and ethanol formation.

SUMMARY OF THE INVENTION

This invention concerns a method for making alkanols and esters which comprises reacting a mixture of CO and $H_2$ at a pressure of about 500 psig or greater and at a temperature of at least 150° C. in the presence of a catalyst system comprising a ruthenium-containing compound, a nickel or iron containing compound and a quaternary phosphonium salt, in the presence of an inert, oxygenated solvent.

DETAILED DESCRIPTION OF THE INVENTION

In the narrower and more preferred practice of this invention, alkanols, especially methanol and ethanol, are prepared by reacting a mixture of CO and $H_2$ at a temperature of about 180° C. to about 250° C. and at a pressure of 2000 psig or greater in the presence of a catalyst system comprising one or more ruthenium-containing compounds, a nickel or iron-containing compound, and a quaternary phosphonium salt, in the presence of an inert, oxygenated solvent such as 1,4-dioxane.

As previously pointed out, the catalyst system employed in the practice of this invention contains one or more ruthenium-containing compounds and a nickel or iron containing compound together with a quaternary phosphonium salt. The ruthenium-containing catalyst, as well as the nickel or iron containing catalyst may be chosen from a wide variety of organic or inorganic compounds, complexes, etc., as will be shown and illustrated below. It is only necessary that the catalyst precursor actually employed contain the said metals in any of their ionic states. The actual catalytically active species is then believed to comprise ruthenium and nickel or iron in complex combination with, for example, tetraalkylphosphonium bromide as well as carbon monoxide and hydrogen.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium dioxide hydrate, ruthenium tetraoxide, anhydrous ruthenium(IV) oxide, ruthenium acetate, ruthenium(III) acetylacetonate, and triruthenium dodecacarbonyl.

The nickel and iron catalyst precursors may take many different forms. For instance, the nickel or iron may be added to the reaction mixture in an oxide form, as in the case of, for example, of iron(II) oxide, iron(III) oxide, or nickel(II) oxide. Alternatively, they may be added as salts of a mineral acid, as in the case of iron(II) nitrate and iron(II) sulfate, as the salt of a suitable organic carboxylic acid, for example, iron(II) acetate, iron(III) acetate and iron oxalate, or as the complex of a carbonyl-containing ligand, as in the case of nickel(II) acetylacetonate, etc. Nickel and iron carbide, carbonate, carbonyl, halide and hydrocarbonyl derivatives such as nickel carbide, iron chloride, nickel(II) chloride, and nickel(II) iodide are also effective catalyst precursors.

Preferred nickel and iron-containing compounds include halides such as nickel chloride or iron chloride, complexes of carbonyl-containing ligands such as nickel(II) acetylacetonate, nickel and iron carbonyls such as nickel carbonyl, iron nonacarbonyl and iron pentacarbonyl, as well as salts of organic acids such as nickel(II) acetylacetonate.

In another embodiment of the process of this invention, the iron and nickel-containing compounds are added as cyclopentadienyl derivatives such as cyclopentadienyl iron dicarbonyl dimer, bis(cyclopentadienyl)nickel and ferrocene.

Quaternary phosphonium salts suitable for use in this invention have the formula:

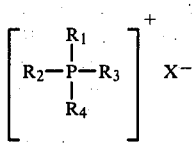

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory in this instance.

Equally useful are the phosphonium salts containing phosphorus bonded to a mixture of alkyl aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus atom through the aryl function.

Illustrative examples of suitable quaternary phosphonium salts include tetrabutylphoshonium bromide, heptyltriphenylphosphonium bromide, tetrabutylphosphonium iodide, tetrabutylphosphonium chloride, tetrabutylphosphonium nitrate, tetrabutylphosphonium chromate, tetrabutyphosphonium tetrafluoroborate and tetrabutylphosphonium acetate.

The preferred quaternary salts are generally the tetralkylphosphonium salts containing alkyl groups having 1-6 carbon atoms, such as methyl, ethyl, and butyl. Preferred tetrabutylphosphonium salts include the chloride, iodide, acetate and chromate salts. Tetrabutylphosphonium salts, such as tetrabutylphosphonium bromide, are most preferred for the practice of this invention. Mixtures of these quaternary salts may also be employed, if desired.

Generally, in the catalyst system the molar ratio of the ruthenium compound to the quaternary phosphonium salt will range from about 1:0.01 to about 1:100 or more and, preferably, will be from about 1:1 to about 1:20.

The quantity of ruthenium compound and the nickel or iron-containing compound employed in the instant invention is not critical and may vary over a wide range. In general, the novel process is desirably conducted in the presence of a catalytically effective quantity of the active ruthenium species and of the nickel or iron species which gives the desired product in reasonable yield. The reaction proceeds when employing as little as about $1 \times 10^{-6}$ weight percent, and even lesser amounts, of ruthenium together with about $1 \times 10^{-6}$ weight percent or less of nickel or iron, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-3}$ to about 10 weight percent in conjunction with a nickel or iron concentration of from about $1 \times 10^{-3}$ to about 10 weight percent, based on the total weight of reaction mixture is generally desirable in the practice of this invention. The preferred ruthenium to iron or nickel atomic ratio is from about 10:1 to about 0.1:1. Mixtures of the nickel and iron containing compounds may be employed in the catalyst system, if desired.

The choice of a suitable solvent is important, especially when a large scale, continuous phase reactor is used. A homogeneous solution must be obtained so that a continuous catalyst feeding is feasible. The solvents useful in the process of this invention are oxygenated hydrocarbons i.e., compounds composed of carbon, hydrogen and oxygen in which the only oxygen atoms present are in ether group, ester groups, ketone group or hydroxyl groups of alcohols. Generally, the oxygenated hydrocarbon will contain 3 to 12 carbon atoms. The solvent must be substantially inert under reaction conditions and it must be one which has a normal boiling point of at least 40° C. at atmospheric pressure and preferably, the solvent will have a boiling point greater than that of ethanol and other oxygen-containing reaction products so that recovery of the solvent by distillation is facilitated.

Preferred ester-type solvents are the aliphatic and acylic carboxylic acid monoesters as exemplified by butyl acetate, methyl benzoate, isopropyl iso-butyrate and propyl propionate as well as dimethyl adipate. Useful alcohol-type solvents include monohydric alcohols such as cyclohexanol, 1-hexanol, neopentanol, 2-octanol, etc. Suitable ketone-type solvents include, for example, cyclic ketones, such as cyclohexanone and 2-methylcyclohexanone, as well as acyclic ketones such as 2-pentanone, butanone, acetophenone, etc. Ethers which may be utilized as solvents include cyclic, acrylic and heterocyclic materials. Preferred ethers are the heterocyclic ethers as illustrated by 1,4-dioxane and 1,3-dioxane. Other suitable ether solvents include di-n-propyl ether, diethylene glycol dibutyl ether, dibutyl ether, ethyl butyl ether, diphenyl ether, heptyl phenyl ether, anisole, tetrahydrofuran, etc. The most useful solvents of all of the above group include the ethers as represented by monocyclic, heterocyclic ethers such as 1,4-dioxane, etc.

The temperature range which can usefully be employed in these syntheses is a variable dependent upon other experimental factors, including the pressure, the concentration and choice of the particular species of ruthenium and iron or nickel catalysts among other things. The range of operability is from about 150° C. to 350° C. when superatmospheric pressures of synthesis gas are employed. A narrow range of 180° to 250° C. represents the preferred temperature range.

Superatmospheric pressures of about 500 psi or greater lead to substantial yields of alkanols by the process of this invention. A preferred operating range is from 2000 psi to 8000 psi, although pressures above 8000 psi also provide useful yields of the desired alkanols.

The relative amounts of carbon monoxide and hydrogen which may be initially present in the syngas, i.e., synthesis gas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxylic acids may also be formed during the course of this alkanol synthesis. Most often these are ester derivatives of acetic acid such as methyl acetate, ethyl acetate, etc. These esters and the individual alkanols formed which include ethanol, propanol and butanol in addition to methanol can be conveniently recovered from the reaction mixture by distillation, extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanol product, and said material may be recovered by methods well known in the art, such as distillation, fractionation, extraction and the like. A fraction rich in the ruthenium and nickel and/or iron catalyst components may then be recycled to the reaction zone, if desired, and additional products generated.

The products have been identified in this work by one or more of the following analytical procedures, viz, gas-liquid chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Selectivity to individual aliphatic oxygenated products in the crude liquid product has been estimated in this work using the equation:

$$\text{selectivity} = \left(\frac{X}{100 - S}\right) \times 100\%$$

where

X = wt% concentration of the individual product in the crude liquid product as determined by glc.
S = wt% concentration of solvent in the crude liquid product as determined by glc.

The product weight gain was estimated, in grams, as the weight difference between the crude liquid product and the total solvent plus catalyst charged at the start of the run.

Various embodiments of the process of this invention are illustrated in the following examples which are to be considered not limitative.

COMPARATIVE EXAMPLE I

This Example illustrates a synthesis of a mixture of alkanols and esters where the reaction of carbon monoxide and hydrogen is catalyzed by ruthenium together with tetrabutylphosphonium bromide salt and where the reaction is conducted in the presence of 1,4-dioxane. There is no second metal involved in this comparative example.

In the examples to follow an effect on product selectivity and/or any increase in yield of alkanols and esters will be observed with the use of a second transition metal catalyst.

To a glass liner was charged hydrated ruthenium oxide (0.19 g, 1.0 mmole), tetra-n-butylphosphonium bromide (3.4 g, 10 mmoles), and 1,4-dioxane (10 g). The glass liner was placed in a stainless steel reactor and purged of air with hydrogen and carbon monoxide (1:1 molar ratio), then pressured to 1000 psi, and heated to 200° C. The pressure was brought up to 6300 psi and during the reaction period the constant pressure was maintained by using a surge tank. After 18 hours, the reactor was allowed to cool, the excess gas sampled and vented and the liquid products recovered.

The liquid products, which were obtained with 8.5 g weight gain, were analyzed by glc and the following product selectivities (on solvent-free basis) were obtained:

| methanol | 43 wt % |
|---|---|
| ethanol | 24 wt % |
| n-propanol | 7 wt % |
| n-butanol | 8 wt % |
| methyl acetate | 3 wt % |
| ethyl acetate | 3 wt % |
| n-propyl acetate | 0 wt % |

Catalyst productivity (based on weight gain) = 8500 g/g-atm-Ru. A typical off-gas analysis showed the presence of:

| carbon monoxide | 36% |
|---|---|
| hydrogen | 41% |
| carbon dioxide | 17% |
| methane | 3.4% |

The water content in the liquid product (Karl-Fischer titration) was 0.75%.

It is realized that methanol is the major component in the liquid product distribution and the ratio of methanol to ethanol is about 1.8:1 (43 wt% vs. 24 wt%)

EXAMPLE II

This Example illustrates a typical synthesis of a mixture of methanol-rich alkanols where the reaction of carbon monoxide and hydrogen is catalyzed by ruthenium together with an iron-containing compound and tetrabutylphosphonium bromide salt and where the reaction is conducted in the presence of 1,4-dioxane.

To a glass liner was charged hydrated ruthenium oxide (0.19 g, 1.0 mmole), tetra-n-butylphosphonium bromide (3.4 g, 10 mmoles), iron nonacarbonyl, (0.09 g, 0.25 mmole) and 1,4-dioxane (10 g). The glass liner was placed in a stainless steel reactor and purged of air with hydrogen and carbon monoxide (1:1 molar ratio), then pressured to 2000 psi, and heated to 220° C. The pressure was brought up to 7800 psig and during the reaction period the constant pressure was maintained by using a surge tank. After 16 hours, the reactor was allowed to cool, the gas pressure (3000 psi) noted, the excess gas sampled and vented and the liquid products recovered.

The liquid products, which were obtained with a 4.0 g weight gain, were analyzed by glc and Karl-Fischer titration and the following product selectivities (solvent-free basis) were obtained:

| methanol | = | 50 wt % |
|---|---|---|
| ethanol | = | 22 wt % |
| n-propanol | = | 1 wt % |
| n-butanol | = | 6 wt % |
| methyl acetate | = | 6 wt % |
| ethyl acetate | = | 2 wt % |
| water | = | 0.8 wt % |

In Examples III and Example IV, to follow, the same reactants were used, in the same molar ratio for ruthenium-containing compound, quaternary salt and iron-containing compound, but the differences lie in iron species, pressures used and the molar ratios of CO/H$_2$. It is realized that varied methanol/ethanol combined selectivities and their relative ratio were obtained.

EXAMPLE III

In Example III a glass liner was charged with hydrated ruthenium oxide (0.19 g, 1.0 mmole), tetra-n-butylphosphonium bromide (3.4 g, 10 mmoles), cyclopentadienyliron dicarbonyl dimer (0.090 g, 0.25 mmole) and 1,4-dioxane (10 g). The glass liner was placed in a stainless steel reactor and purged of air with hydrogen and carbon monoxide (1:1 molar ratio), then pressured to 1000 psi and heated to 220° C. The pressure fluctuated between 3280 and 6275 psi during the reaction period. After 18 hours, the reactor was allowed to cool, the gas pressure noted (1840 psig), the excess gas sampled and vented and the liquid products recovered.

The liquid products were analyzed by glc and Karl-Fischer titration and the following product selectivities were obtained:

| methanol | = | 34 wt % |
|---|---|---|
| ethanol | = | 34 wt % |
| n-propanol | = | 7 wt % |
| n-butanol | = | 3 wt % |
| methyl acetate | = | 9 wt % |
| ethyl acetate | = | 7 wt % |
| water | = | 0.32 wt % |

EXAMPLE IV

Example IV was conducted the same as Example III in every respect, except after initially pressuring to 1000 psig, the pressure was brought up to 6300 psi and was maintained constant at that level for 18 hours by use of a surge tank. Additionally, the molar ratio of CO/H$_2$ was 1:2 instead of 1:1.

After 18 hours, the reactor was allowed to cool, the gas pressure noted, the excess gas sampled and vented and the liquid products recovered.

The liquid products, which were obtained with a 4.2 g weight gain were analyzed by glc and Karl-Fischer titration and the following product selectivities were obtained:

| methanol | = | 77 wt % |
|---|---|---|
| ethanol | = | 11 wt % |
| n-propanol | = | 3 wt % |
| n-butanol | = | 4 wt % |
| methyl acetate | = | 1 wt % |
| ethyl acetate | = | 3 wt % |

It will be noted that these conditions are highly selective for methanol (77%) and also for C$_1$ to C$_4$ alkanols (95%).

EXAMPLE V

Here, a glass liner was charged with hydrated ruthenium oxide (0.19 g, 10 mmoles), nickel(II) chloride (0.064 g, 0.25 mmole) and 1,4-dioxane (10 g). The glass liner was placed in a stainless steel reactor and purged of air with hydrogen and carbon monoxide (1:1 molar ratio), then pressured to 1000 psi, and heated to 220° C. The pressure was brought up to 6300 psi and during the reaction period the constant pressure was maintained by use of a surge tank. After 18 hours, the reactor was allowed to cool, the gas pressure (3240 psi) noted, the excess gas sampled and vented and the liquid products recovered.

The liquid products, which were obtained with a 3.2 g weight gain, were analyzed by glc and Karl-Fischer titration and the following selectivities were obtained:

| methanol | = | 29 wt % |
|---|---|---|
| ethanol | = | 33 wt % |
| n-propanol | = | 6 wt % |
| n-butanol | = | 5 wt % |
| methyl acetate | = | 12 wt % |
| ethyl acetate | = | 9 wt % |
| water | = | 0.4 wt % |

EXAMPLE VI

In Example VI the same method was used as in Examples II, III and V. Differences included the use of bis(cyclopentadienyl) nickel (0.047 g, 0.25 mmole) as the second metal catalyst and a constant pressure maintained at 5900 psi, after the initial increase to 1000 psi.

The liquid products, which were obtained with a 7.4 g weight gain, were analyzed by glc and Karl-Fischer titration and the following selectivities were obtained:

| methanol | = | 44 wt % |
|---|---|---|
| ethanol | = | 24 wt % |
| n-propanol | = | 5 wt % |
| n-butanol | = | 3 wt % |
| methyl acetate | = | 0 wt % |
| ethyl acetate | = | 0 wt % |

EXAMPLE VII

Again, the same method was used as in previous Examples II, IV, and V, but the nickel catalyst was in the form of nickel(II) acetylacetonate (0.064 g, 0.25 mmole), and after pressuring to 1000 psi, the pressure was increased to 6000 psi and maintained constant by use of a surge tank.

The liquid products showed a 5.9 g weight gain and glc analysis indicated the following product distribution:

| | | | |
|---|---|---|---|
| methanol | = | 46 | wt % |
| ethanol | = | 20 | wt % |
| n-propanol | = | 3 | wt % |
| n-butanol | = | 9 | wt % |
| methyl acetate | = | 7 | wt % |
| ethyl acetate | = | 3 | wt % |

EXAMPLE VIII

A glass liner was charged with hydrated ruthenium oxide (0.19 g, 1 mmole), tetra-n-butylphosphonium bromide, (3.4 g, 10 mmoles), nickel iodide, (0.156 g, 0.5 mmole) and 1,4-dioxane (10 g). The glass liner was placed in a stainless steel reactor and purged of air with hydrogen and carbon monoxide (1:1 molar ratio), then pressured to 1000 psi and heated to 220° C. The pressure was increased to 6400 psi and maintained constant for 18 hours by means of a surge tank. After 18 hours, the reactor was allowed to cool, the gas pressure noted, the excess gas sampled and vented and the liquid products recovered.

The liquid products recovered showed a 6.9 g weight gain. When analyzed by glc and Karl-Fischer titration the following results were obtained:

| | | | |
|---|---|---|---|
| methanol | = | 34 | wt % |
| ethanol | = | 37 | wt % |
| n-propanol | = | 6 | wt % |
| n-butanol | = | 0 | wt % |
| methyl acetate | = | 8 | wt % |
| ethyl acetate | = | 6 | wt % |
| water | = | 0.73 | wt % |

EXAMPLE IX

This Example was conducted the same as Example VIII, except the pressure was maintained constant at 4500 psi for 18 hours, instead of 6400 psi. The same method of analysis showed a 3.2 g weight gain and showed the following products:

| | | | |
|---|---|---|---|
| methanol | = | 42 | wt % |
| ethanol | = | 39 | wt % |
| n-propanol | = | 4 | wt % |
| n-butanol | = | 0 | wt % |
| methyl acetate | = | 5 | wt % |
| ethyl acetate | = | 4 | wt % |
| water | = | 3.6 | wt % |

These examples have demonstrated the product distributions, especially the methanol/ethanol ratio, are affected by the addition of various second metals used.

It is claimed:

1. A process for making alkanols which comprises reacting a mixture of CO and $H_2$ at a pressure of about 500 psig or greater and at a temperature of at least 150° C. in the presence of a catalyst system comprising a ruthenium-containing compound, a material selected from the group consisting of a nickel-containing compound or an iron-containing compound and a quaternary phosphonium salt, in the presence of an inert, oxygenated solvent.

2. The process of claim 1 wherein the process is conducted at a pressure of about 2000 psi to about 8000 psi.

3. The process of claim 1 wherein the process is conducted at a temperature of about 150° to about 350° C.

4. The process of claim 1 wherein the process is conducted at the ratio of CO to $H_2$ of about 1:5 to 5:1.

5. The process of claim 1 wherein said quaternary salt is tetraalkylphosphonium salt.

6. The process of claim 5 wherein said alkyl groups contain 1-6 carbon atoms.

7. The process of claim 1 wherein said quaternary salt is a mixed alkaryl phosphonium salt.

8. The process of claim 6 wherein said quaternary salt is tetrabutylphosphonium salt.

9. The process of claim 8 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

10. The process of claim 9 wherein the said tetrabutylphosphonium salt is tetrabutylphosphonium bromide.

11. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl derivatives.

12. The process of claim 11 wherein the said ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecacarbonyl.

13. The process of claim 12 wherein said ruthenium-containing compound is ruthenium(IV) dioxide hydrated.

14. The process of claim 12 wherein said ruthenium-containing compound is ruthenium carbonyl.

15. The process of claim 1 wherein the said nickel-containing compound is selected from the group consisting of nickel oxide, nickel chloride, nickel iodide, nickel acetylacetonate, bis(cyclopentadienyl) nickel, and nickel carbonyl.

16. The process of claim 1 wherein the said nickel-containing compound is nickel chloride.

17. The process of claim 1 wherein the said iron-containing compound is selected from the group consisting of iron nonacarbonyl, iron(III) acetylacetonate, iron(II) chloride, iron(II) oxide, iron(III) oxide, ferrocene, iron pentacarbonyl, and cyclopentadienyl iron dicarbonyl dimer.

18. The process of claim 1 wherein the said iron-containing compound is iron nonacarbonyl.

19. The process of claim 1 wherein the said iron-containing compound is iron chloride.

20. The process of claim 1 wherein the said catalyst system also contains a cyclopentadienyl ligand.

21. The process of claim 1 wherein the said solvent is selected from the group consisting of 1,3-dioxane, 1,4-dioxane, and diphenyl ether.

22. The process of claim 1 wherein the said solvent is 1,4-dioxane.

* * * * *